United States Patent [19]

Van Snick et al.

[11] Patent Number: 5,208,218
[45] Date of Patent: May 4, 1993

[54] T CELL GROWTH FACTOR GLYCOPROTEINS

[75] Inventors: Jacques Van Snick, Brussels; Catherine Uyttenhove, Chaumont-Gistoux, both of Belgium; Richard J. Simpson, Melbourne, Australia

[73] Assignee: Ludwig Institute for Cancer Research, New York, Switzerland

[21] Appl. No.: 246,482

[22] Filed: Sep. 19, 1988

[51] Int. Cl.⁵ .................. A61K 37/36; C07K 15/14
[52] U.S. Cl. ............................ 514/8; 514/12; 514/21; 530/395; 530/397; 530/399; 530/351; 424/85.1; 930/141; 930/140
[58] Field of Search ............ 530/395, 397, 399; 514/21, 8, 12

[56] References Cited

U.S. PATENT DOCUMENTS 5,006,459 4/1991 Kung .................................. 530/395

FOREIGN PATENT DOCUMENTS 0361284 4/1990 European Pat. Off. .
901432 11/1990 PCT Int'l Appl. .

OTHER PUBLICATIONS

Yang et al., blood 74(6): 1880–1884 (Nov. 1, 1989).
Renauld et al., Cytokines 2(1): 9–12 (Jan. 1990).
Renauld et al., J. Immunol. 144(11): 4235–4241 (Jun. 1990).
Druez et al., J. Immunol. 145(8): 2494–2499 (Oct. 1990).

Primary Examiner—Fatemeh T. Moezie
Attorney, Agent, or Firm—Felfe & Lynch

[57] ABSTRACT

The present invention relates generally to a T cell growth factor. More particularly, the present invention relates to a T cell growth factor which comprises a glycoprotein which supports interleukin 2- and interleukin 4-independent growth of helper T cells. Even more particularly, the present invention relates to the helper T cell growth factor P40, pharmaceutical compositions thereof and antibodies thereto. The present invention also contemplates a method for inducing the proliferation of helper T cells. The helper T cell growth factor contemplated herein is useful in the stimulation of specific cells in the immune system.

6 Claims, 5 Drawing Sheets

FIG. 4B

| 1 | 2 | 3 | 4 | kDa |
|---|---|---|---|---|
| | | | | —94 |
| | | | | —67 |
| | | | ● | —43 |
| | | | | —30 |
| | | | | —20 |
| | | | | —14 |

T CELL GROWTH FACTOR GLYCOPROTEINS

FIELD OF THE INVENTION

The present invention relates generally to a T cell growth factor. More particularly, the present invention relates to a mammalian T cell growth factor which comprises a glycoprotein which supports interleukin 2- and interleukin 4-independent growth of helper T cells. Even more particularly, the present invention relates to the helper T cell growth factor P40, pharmaceutical compositions thereof and antibodies thereto. The present invention also contemplates a method for inducing the proliferation of helper T cells. The helper T cell growth factor contemplated herein is useful in the stimulation of specific cells in the immune system.

BACKGROUND OF THE INVENTION

Many cytokines are polypeptides which directly or indirectly mediate host defense mechanisms and/or which mediate tissue growth differentiation. Cytokines have been recognized which mediate host defense against cancer and/or infection. Such cytokines include the interferons (IFN-α, IFN-β and IFN-γ), tumor necrosis factor (TNF-α), lymphotoxin (TNF-β), the interleukins (IL-1, 2, 3, 4, 5 and 6), leukoregulin, natural killer cell cytotoxic factor (NKCF), transforming growth factor (TGF), colony stimulating factors (CSF) such as macrophage (M-CSF), granulocyte (G-CSF) and macrophage, granulocyte-CSF (G,M-CSF), and oncostatin M. Each of the aforementioned cytokines have unique characteristics and a unique range of anti-proliferative, cytostatic, antiviral or growth regulatory activity.

Several cytokines are synthesized by leukocytes, commonly in response to stimulation by microorganisms, antigens or mitogens. This has been observed in vitro. Following this stimulation in cell culture, the supernatant fluid is retrieved and cytokine activity identified, isolated and further characterized. In recent years, it has become increasingly clear that IL-2 is not the only factor controlling T cell growth. Indeed, several cytokines, including IL4 (Fernandez-Botran et al., Proc. Natl. Acad. Sci. USA 83:9689-9693, 1986; Lichtman et al., Proc. Natl. Acad. Sci. USA 84:824-827, 1987), G,M-CSF (Woods et al., J. Immunol. 138:4293-4297, 1987; Kupper et al., J. Immunol. 138:4288-4292, 1987) and, in a human system, the combination of IL1 and IL6 (Houssiau et al. Eur. J. Immuno., 18: 653-656, 1988), have now been shown to induce IL-2-independent T cell proliferations. Consequently, the regulation of T cell growth is more complex than originally thought, although IL-2 is a potent and broadly active T cell growth factor.

An important subset of T cell is the helper T cell ($T_H$). At least two types of helper T cell have been identified on the basis of functional criteria. One type of $T_H$ cell ($T_H1$) helps B cells in a linked, antigen-specific manner, and is required early in the response. Another type of $T_H$ ($T_H2$) helps B cells in a nonlinked manner and is required later in the response.

Several years ago, a collection of helper T cell lines from lymph nodes of antigen-primed mice was obtained using the procedure described by Corradin et al., J. Immunol. 119:1048-1053, 1977. These cell lines were initiated by culture in the presence of antigen and were subsequently maintained, without addition of exogenous growth factors, by regular feeding with antigen and irradiated splenic antigen-presenting cells. Most of these cells produce large amounts of IL3, IL4, IL5 and IL6 but no IL2 and, therefore, belong to the $T_H2$ type defined by Mosmann et al. J. Immunol. 136:2348-2357, 1986.

In accordance with the present invention, it is surprisingly discovered that two clones derived from the above-mentioned cell lines proliferated in response to their own conditioned medium in the absence of antigen and feeder cells. The subject invention relates to a novel T cell growth factor distinct from other known cytokines. The new growth factor is useful as a therapeutic compound to stimulate proliferation of helper T cells.

SUMMARY OF THE INVENTION

The present invention is directed to a mammalian T cell growth factor which comprises a protein which supports interleukin 2-independent and interleukin 4-independent growth of helper T cells.

More particularly, the present invention relates to a T cell growth factor having the identifiable characteristics of P40 and derivatives thereof.

Another aspect of the present invention relates to a pharmaceutical composition comprising an effective amount of P40 or a derivative thereof and a pharmaceutically acceptable carrier useful in the stimulation of specific cells in the immune system.

Still another aspect of the present invention relates to antibodies specific to P40 or an antigenic derivative thereof useful in diagnostic assays for P40.

Yet another aspect of the present invention relates to a recombinant DNA molecule encoding the polypeptide portion of P40 or a derivative thereof thereby providing a convenient source of recombinant P40.

Still yet another aspect of the present invention contemplates a method of proliferating helper T cells which comprises incubating said cells with a proliferating effective amount of P40 or a derivative thereof for a time and under conditions sufficient for said cells to proliferate.

The shaded area in FIG. 2A to 2D represent P40 activity.

Figure 3:
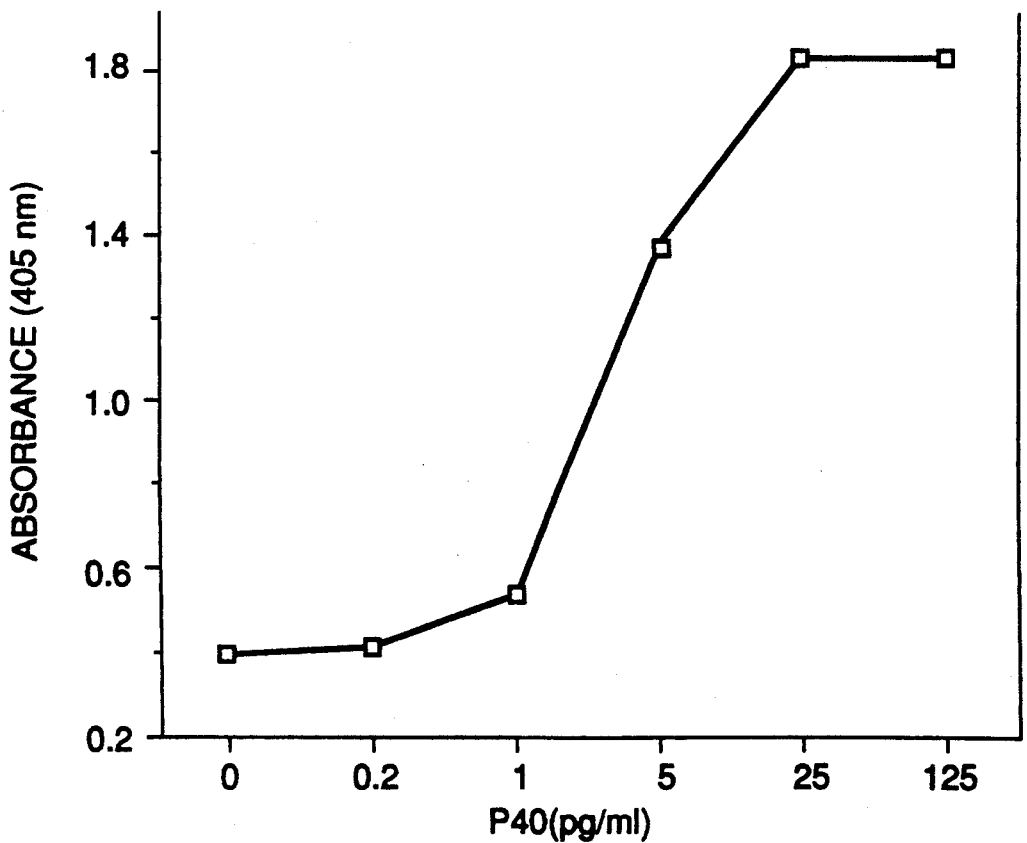

FIG. 3 is a graphical representation depicting growth factor activity of purified P40. TS1cells ($3 \times 10^3$ cells/well) are cultivated in presence of increasing doses of purified P40. After 3 days, cell numbers are evaluated by measuring hexosaminidase levels.

Figure 4A:
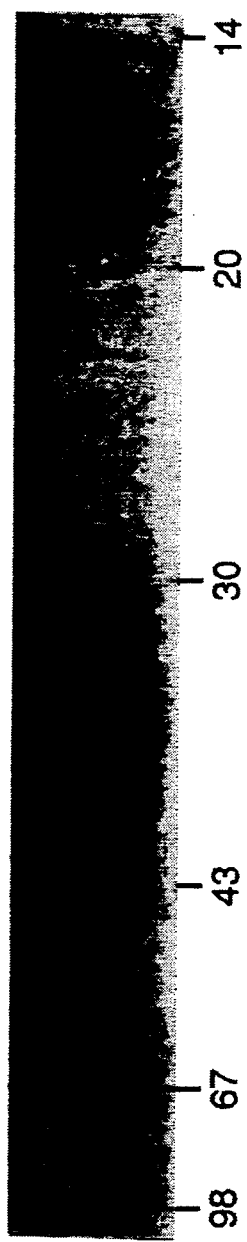

FIG. 4a shows a photograph of silver stained Na DodSO4/PAGE gel studies on purified P40. The studies were carried out under reducing conditions.

Figure 4B:
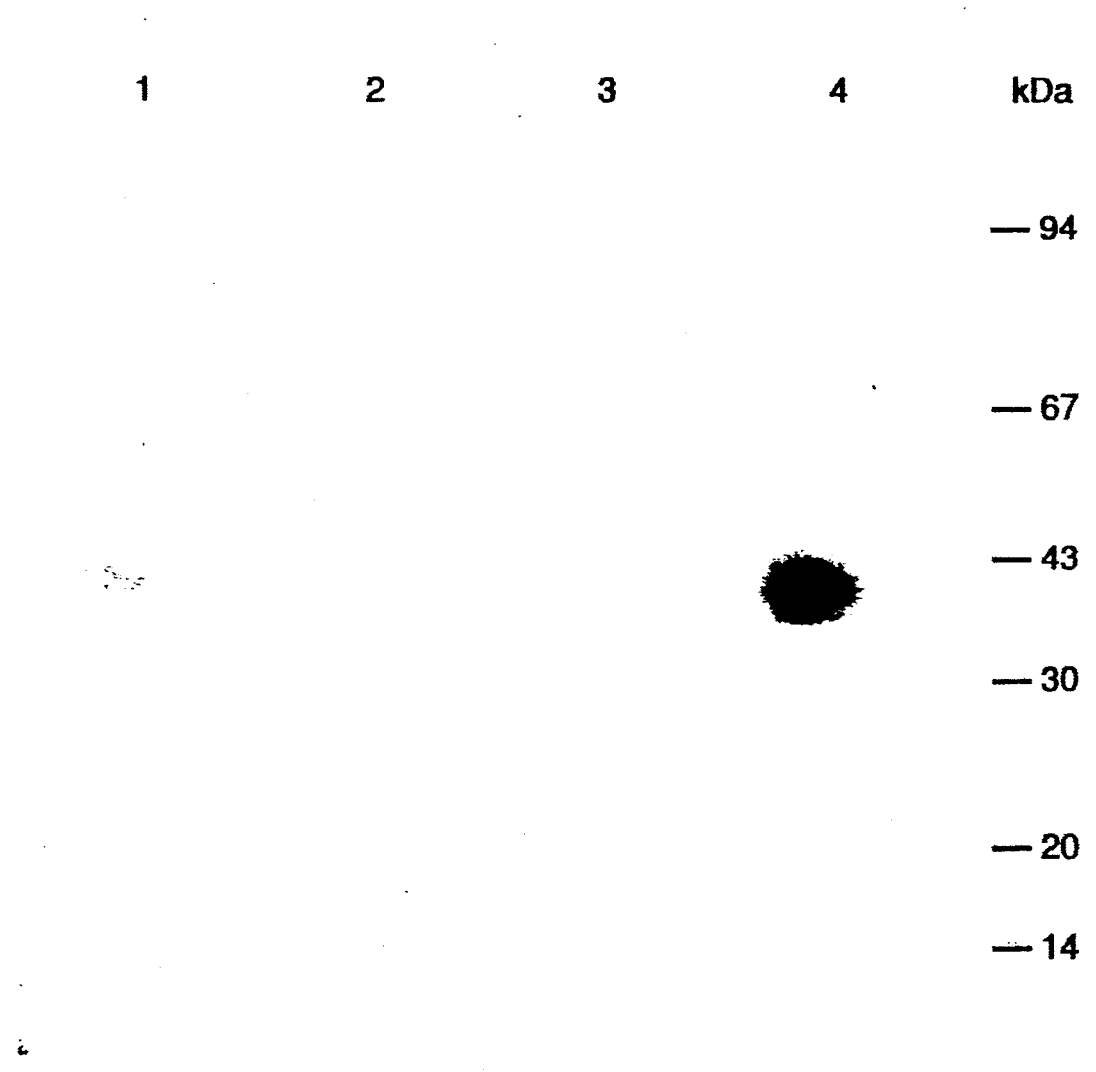

FIG. 4b also shows gel studies on purified P40.

DETAILED DESCRIPTION OF THE INVENTION

The present invention relates to a mammalian T cell growth factor which comprises a protein which supports, or is capable of supporting, interleukin 2 (IL2)-independent and interleukin 4 (IL4)-independent growth of helper T cells in the absence of antigen. In accordance with the present invention and using the methods contained herein, said T cell growth factor is biologically pure. By biologically pure is meant a composition comprising said T cell growth factor. The composition may comprise homogeneous T cell growth factor or may consist essentially of T cell growth factor. As used in the specification and appended claims, supporting IL2-independent and IL4-independent growth of helper T cells refers to the ability for said cells to proliferate in the absence of IL2 and/or IL4. This feature distinguishes the subject growth factor from others presently known. In accordance with the present invention, this ability is due to a novel and heretofore unknown T cell growth factor. Hereinafter, said growth factor is referred to as P40. As defined herein, derivatives of P40 encompass synthetic and naturally occurring amino acid substitutions, deletions and/or insertions as will be apparent to the skilled artisan. For example, non-essential amino acid deletions, i.e., deletion of amino acids which do not affect the activity of P40 are obtainable by genetic engineering means. An antigenic derivative of P40 is defined to be a portion of P40 which is capable of reacting with an antibody specific to P40. All such derivatives are encompassed by the subject invention.

Accordingly, P40 is a protein, and more particularly a glycoprotein, capable of supporting long term IL2-independent and IL4-independent growth of helper T cell lines in the absence of antigen, and is isolated from helper T cell lines. P40 is functionally distinct from all known interleukins and colony-stimulating factors. P40 is purified from the supernatant (SN) of lectin-stimulated mouse helper T cell lines to a specific activity of from about 10 U/mg to about $10^{10}$ U/mg but generally to about $10^8$ U/mg and characterized as a basic (pI 10) single chain protein with a Mr of from about 30 to about 40 kDa. Two observations indicate that P40 is a glycoprotein: (i) its heterogeneous migration pattern in NaDodSO4/PAGE and (ii) its binding to lentil lectin, which points to the presence of N-linked carbohydrate side chains. Consistent with this observation, a number of potential N-glycosylation sites (Asn-X-Thr motif) have been identified in the protein sequence determination. Moreover, additional evidence for extensive glycosylation of the molecule is obtained in experiments with N-glycanase treatment, which reduced the Mr of P40 to about 15 kDa. P40 is a stable molecule whose biological activity is not altered after exposure to NaDodSO4, acid pH, or acetonitrile. By contract, its activity is destroyed by 2-mercaptoethanol, which suggests that intramolecular disulfide bridges play on important role in maintaining appropriate folding of the molecule. P40 is also distinguished from known proteins on the basis of its complete amino acid sequence deduced from a cDNA clone and confirmed by amino acid sequencing. The DNA and amino acid sequence comprises:

```
                        -18                                                      -10
                        Met Leu Val Thr Tyr Ile Leu Ala Ser Val Leu Leu Phe Ser Ser
     5' CAGACTCCCGTCAACATGTTGGTGACATACATCCTTGCCTCTGTTTTGCTCTTCAGTTCT 1                                                    100
          Val Leu Gly Gln Arg Cys Ser Thr Thr Trp Gly Ile Arg Asp Thr Asn Tyr Leu Ile Glu
          GTGCTGGGCCAGAGATGCAGCACCACATGGGGCATCAGAGACACCAATTACCTTATTGAA
                                                100

20                                    30
          Asn Leu Lys Asp Asp Pro Pro Ser Lys Cys Ser Cys Ser Gly Asn Val Thr Ser Cys Leu
          AATCTGAAGGATGATCCACCGTCAAAATGCAGCTGCAGCGGCAACGTGACCAGCTGCTTG 40                                  50
          Cys Leu Ser Val Pro Thr Asp Asp Cys Thr Thr Pro Cys Tyr Arg Glu Gly Leu Leu Gln
          TGTCTCTCCGTCCCAACTGATGATTGTACCACACCGTGCTACAGGGAGGGACTGTTACAG
                                      200

60                                              70
          Leu Thr Asn Ala Thr Gln Lys Ser Arg Leu Leu Pro Val Phe His Arg Val Lys Arg Ile
          CTGACCAATGCCACACAGAAATCAAGACTCTTGCCTGTTTTCCATCGGGTGAAAAGGATA
                                                                      300

80                                 90
          Val Glu Val Leu Lys Asn Ile Thr Cys Pro Ser Phe Ser Cys Glu Lys Pro Cys Asn Gln
          GTTGAAGTCCTAAAGAACATCACGTGTCCGTCCTTTTCCTGCGAAAAGCCATGCAACCAG 100                              110
          Thr Met Ala Gly Asn Thr Leu Ser Phe Leu Lys Ser Leu Leu Gly Thr Phe Gln Lys Thr
          ACCATGGCAGGCAACACACTGTCATTTCTGAAGAGTCTCCTGGGGACGTTCCAGAAGACA
                                                    400

120              126
          Glu Met Gln Arg Gln Lys Ser Arg Pro
          GAGATGCAAAGGCAGAAAAGCCGACCATGAAGACAGATGCTATTTATTCTATTTATTGAA
          TTTACAAAACCTCCCCTCCTTAACTGTTACAGTGAAGAAATAAACTAAGCTATTCT 3'
                            500
```

In addition to the aforementioned distinguishing structural characteristics of P40, it also differs functionally from IL2. P40 is completely inactive on cytolytic T cell clones under conditions where their response to IL2 is very strong; conversely, IL2 fails to support long term antigen independent growth of helper T cell lines, whereas P40 is very active in this system. To date, long term growth of helper cells in response to P40 means greater than two months and may be indefinite. In contrast with these differences, a correlation is observed between the sensitivity of helper T cell lines to P40 and IL4, indicating that T cell activation by these two molecules is similarly regulated. However, the range of activities of IL4, which also stimulates the growth of a variety of IL3-dependent cell lines and of cytolytic T cells (Mosmann et al., *Proc. Natl. Acad. Sci. USA* 83:5654–5658, 1986; Widmer et al., Nature 326:795–798, 1987) is broader than that of P40, indicating that the functional overlap between the two factors, IL4 and P40, is only partial.

Another advantage of the subject T cell growth factor, P40, is the surprising discovery that P40 is specific for helper T cell lines. This indicates the existence of a growth-stimulatory mechanism restricted to the helper T cell subset. Such a mechanism is important for maintaining the balance between the supply of helper T cell products like IL2 and IL4 and their increased consumption by other lymphocytes activated in the course of the immune response.

It is within the scope of the present invention to include biologically pure P40 in addition to homogeneous and heterogeneous compositions thereof. Accordingly, in accordance with the present invention, supernatant (SN) from a helper T cell line not requiring antigen or feeders comprises P40. This SN is able to induce cell proliferation without further requirement for antigen or feeder cells. As further described in Example 1, the proliferation activity is not inhibited by either anti-IL4 or anti-IL2 receptor antibodies, indicating that said activity is mediated neither directly nor indirectly by these molecules. The active ingredient in the aforementioned SN is shown to be in accordance with the present invention, P40. The SN is active on the test cells, TS1, inducing half-maximal proliferation at dilutions ranging of from about $10^{-6}$ to about $10^{-2}$ (v/v) and generally ranging of from about $10^{-5}$ to about $10^{-4}$ (v/v). Accordingly, in accordance with the present invention, the novel T cell growth factor P40 is active in biologically pure form and in homogeneous and heterogeneous compositions. As exemplified herein, SN fluid is a form of heterogeneous composition of P40. Homogeneous compositions are exemplified herein to include pharmaceutical compositions and the like.

The T cell growth factor P40 is contemplated herein to be useful in stimulating the proliferation of T helper cells in mammals. In a preferred embodiment, P40 is particularly useful in stimulating certain subsets of T helper cells in mammals. Accordingly, P40 is a new and useful therapeutic compound capable of stimulating specific cells within the immune cells. For example, this is particularly important for human patients carrying defects in certain subsets of T helper cells as may be the case with various AIDS patients or immune compromise patients. It should also be noted that of the many advantages of the present invention, the proliferation of helper T cells by P40 will have the additional effect of allowing increased amounts of other cytokines to be produced. Accordingly, the present invention also contemplates a method of treatment of immune deficiency comprising the administration of a proliferating effective amount of P40, or an active derivative, for a time and under conditions sufficient to effect proliferation of helper T cells. In accordance with the present invention, the time required for the proliferation of helper T cells ranges from about two days to about seven days.

Accordingly, the subject invention contemplates a method for inducing and maintaining the proliferation of helper T cells, and preferably, certain subsets thereof, in a mammal which comprises administering to said mammal a proliferating effective amount of a pharmaceutical composition containing P40 for a time and under conditions sufficient for said cells to proliferate. Additionally, a method for inducing and maintaining the proliferation of helper T cells, and preferably certain subsets thereof, in a mammal, is contemplated by this invention in which a nucleic acid molecule encoding P40 is introduced into a T cell in such a manner that said nucleic acid molecule is expressed intracellularly but extrachromosomally of said cell or following integration into the genome of said cell. In this case, the nucleic acid molecule is carried to said T cell and transferred into said cell by a second nucleic acid molecule (e.g., various viruses). The first nucleic acid molecule is manipulated such that it contains the appropriate signals for expression. That is, in accordance with the present invention, a method for proliferating T helper cells in a mammal is contemplated comprising administering a first nucleic acid molecule encoding P40, said nucleic acid molecule being contained in a pharmaceutically acceptable second nucleic acid carrier molecule such that said first nucleic acid molecule enters a T cell and is either maintained extrachromosomally or integrates into the genome of said target all in such a manner that said first nucleic acid molecule is expressed so as to produce an effective amount of P40. By nucleic acid molecule is meant the nucleotide sequence which encodes, directly or indirectly, P40 or a derivative thereof. A nucleic acid molecule is defined herein to mean RNA or DNA.

The active ingredients of a pharmaceutical composition comprising P40, are contemplated to exhibit excellent and effective therapeutic activity, for example, in the treatment of immune compromised diseases in mammals. Thus, the active ingredients of the therapeutic compositions comprising P40 exhibit helper T cell proliferative activity when administered in amounts which depend on the particular disease. For example from about 0.5 ug to about 2000 mg per kilogram of body weight per day may be administered. Dosage regima may be adjusted to provide the optimum therapeutic response. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular, subcutaneous, intranasal, intradermal or suppository routes. Depending on the route of administration, the active ingredients which comprise P40 may be required to be coated in a material to protect said ingredients from the action of enzymes, acids and other natural conditions which may inactivate said ingredients. For example, the low lipophilicity of P40 will allow it to be destroyed in the gastrointestinal tract by enzymes capable of cleaving peptide bonds and in the stomach by acid hydrolysis. In order to administer P40 by other than parenteral administration, P40 will be coated by, or administered with, a material to prevent its inactivation. For example, P40 may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil-in-water P40 emulsions as well conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When P40 is suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 10 ug and 1000 ug of active compound.

The tablets, troches, pills, capsules and the like may also contain the following: A binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 ug to about 2000 mg. Expressed in proportions, the active compound is generally present in from about 10 ug to about 2000 mg/ml of carrier. In the case of compositions containing supplementary active ingredients, the dosages are determined by reference to the usual dose and manner of administration of the said ingredients.

The present invention also relates to antibodies to P40. Such antibodies are contemplated to be useful in developing detection assays (immunoassays) for said P40 especially during the monitoring of a therapeutic regimen and in the purification of P40. The antibodies may be monoclonal or polyclonal Additionally, it is within the scope of this invention to include any second antibodies (monoclonal or polyclonal) directed to the first antibodies discussed above. The present invention further contemplates use of these second antibodies in detection assays and, for example, in monitoring the effect of an administered pharmaceutical preparation. Furthermore, it is within the scope of the present invention to include antibodies to the glycosylated regions of P40, and to any molecules complexed with said P40. Accordingly, in accordance with this invention, an antibody to P40 encompasses antibodies to P40, or antigenic parts thereof, and to any associated molecules (e.g., glycosylated regions, lipid regions, carrier molecules, and the like).

The P40, or parts thereof, considered herein are purified, as exemplified in Example 3, then utilized in antibody production. Both polyclonal and monoclonal antibodies are obtainable by immunization with P40 or its derivative polypeptides, and either type is utilizable for immunoassays. The methods of obtaining both types of sera are well known in the art. Polyclonal sera are less preferred but are relatively easily prepared by injection of a suitable laboratory animal with an effective amount of the purified P40, or parts thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in the present immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Douillard, J. Y. and Hoffman, T., "Basic Facts About Hybridomas", in *Compendium of Immunology*, Vol. II, L. Schwartz (Ed.) (1981); Kohler, G. and Milstein, C. *Nature* 256:495–497 (1975); *European Journal of Immunology*, Vol. 6, pp. 511–519 (1976), Koprowski, et al., U.S. Pat. No. 4,172,124, Koprowski et al., U.S. Pat. No. 4,196,265 and Wands, U.S. Pat. No. 4,271,145, the teachings of which are herein incorporated by reference.

Unlike preparation of polyclonal sera, the choice of animal is dependent on the availability of appropriate immortal lines capable of fusing with lymphocytes thereof. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with from about 1 mg to about 20 mg of the purified P40, or parts thereof. Usually the injecting material is emulsified in Freund's complete adjuvant. Boosting injections may also be required. The detection of antibody production can be carried out by testing the antisera with appropriately labeled antigen. Lymphocytes can be obtained by removing the spleen or lymph nodes of sensitized animals in a sterile fashion and carrying out fusion. Alternatively, lymphocytes can be stimulated or immunized in vitro, as described, for example, in C. Reading *J. Immunol. Meth.*, 53:261–291, 1982.

A number of cell lines suitable for fusion have been developed, and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: $MPC_{11}$-X45-6TG, P3-NS1-1-Ag4-1, P3-X63-Ag8, or mutants thereof such as X63-Ag8.653, SP2-0-Ag14 (all BALB/C derived), Y3-'Ag1.2.3 (rat), and U266 (human).

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1,000 to 6,000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion gives optimum results. The ratio between lymphocytes and malignant cells is optimized to avoid cell fusion among spleen cells and a range of from about 1:1 to about 1:10 gives good results.

The successfully fused cells can be separated from the myeloma line by any technique known by the art. The most common and preferred method is to choose a malignant line which is Hypoxanthine Guanine Phosphoribosyl Transferase (HGPRT) deficient, which will not grow in an aminopterin-containing medium used to allow only growth of hybrids and which is generally composed of hypoxanthine $1.10^{-4}M$, aminopterin $1\times10^5M$, and thymidine $3\times10^{-5}M$, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxanthine, thymidine-containing medium.

The growing colonies are then tested for the presence of antibodies that recognize the antigenic preparation.

Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulines from the inflammatory ascites. Antibody purification may then be achieved by, for example, affinity chromatography.

The presence of P40 contemplated herein, or antibodies specific for same, in a patient's serum, tissue or tissue extract, can be detected utilizing antibodies prepared as above, either monoclonal or polyclonal, in virtually any type of immunoassay. A wide range of immunoassay techniques are available as can be seen by reference to U.S. Pat. Nos. 4,016,043, 4,424,279 and 4,018,653. This, of course, includes both single-site and two-site, or "sandwich", assays of the non-competitive types, as well as in the traditional competitive binding assays. Sandwich assays are among the most useful and commonly used assays and are favored for use in the present invention. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen secondary complex, a second antibody, labeled with a reporter molecule capable of producing a detectable signal is then added and incubated, allowing time sufficient for the formation of a tertiary complex of antibody-antigen-labeled antibody (e.g. antibody-P40-antibody). Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody, or a reverse assay in which the labeled antibody and sample to be tested are first combined, incubated and then added to the unlabeled surface bound antibody. These techniques are well known to those skilled in the art, and then possibly of minor variations will be readily apparent.

In the typical forward sandwich assay, a first antibody having specificity for P40, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of crosslinking covalently binding or physically adsorbing the molecule to the insoluble carrier. Following binding, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten. By "reporter molecule," as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e., radioisotopes). In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, B-galactosidase and alkaline phosphatase, among other. The substrates to be used with the specific enzymes are generally chosed for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above. In all cases, the enzyme-labeled antibody is added to the first antibody hapten complex, allowed to bind, and then to the first antibody hapten complex, allowed to bind, and then the excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose. It will also be apparent that the foregoing can be used to detect directly or indirectly (i.e., via antibodies) the P40 of this invention.

Accordingly, the present invention is also directed to a kit for the rapid and convenient assay of P40 in mammalian body fluids (e.g. serum, tissue extracts, tissue fluids), in vitro cell culture supernatants, and cell lysates. The kit is compartmentalized to receive a first container adapted to contain an antibody to P40, or to an antigenic component thereof, and a second container adapted to contain a second antibody to P40, or to an antigenic component thereof, said second antibody being labeled with a reporter molecule capable of giving a detectable signal as hereinbefore described. If the reporter molecule is an enzyme, then a third container adapted to contain a substrate for said enzyme is provided. In an exemplified use of the subject kit, a sample to be tested for P40 is contacted to the contents of the first container for a time and under conditions for P40, if present, to bind to the antibodies in said first container. After removal of unbound material (e.g. by washing with sterile phosphate buffered saline) the contents of the second is contacted to said first container. If P40 has bound to the antibodies of the first container, the second antibodies of the second container will bind to the secondary complex to form a tertiary complex and, since said second antibodies are labeled with a reporter molecule, when subjected to a detecting means, the tertiary complex is detected.

Another aspect of this invention relates to a recombinant nucleic acid molecule, said molecule defined herein to be DNA or RNA, encoding P40 or parts thereof. In one embodiment, the recombinant nucleic acid molecule is complementary DNA (cDNA). It is considered within the scope of the present invention to include the cDNA molecule encoding mammalian P40, but preferably human P40, or to regions or parts thereof including any base deletion, insertion or substitution or any other alteration with respect to nucleotide sequence or chemical composition (e.g. methylation and glycosylation). P40 encoded by cDNA is referred to herein as recombinant P40.

Methods considered useful in obtaining recombinant P40 cDNA are contained in Maniatis et al., 1982, in *Molecular Cloning: A Laboratory Manual*, Cold Spring Harbor Laboratory, New York, pp. 1-545. Briefly, polyadenylated mRNA is obtained from stimulated helper T cells and fractionated on agarose gels. Optionally, aliquots of mRNA can be injected into *Xenopus laevis* oocytes for translation and assayed for P40 activity using the methods contained herein to enriched fractions of mRNA translating into P40 active molecules. Alternatively, mRNA not enriched is used as template for cDNA synthesis. Libraries of cDNA clones are constructed in the PstI site of the vector pBR322 (using homopolymer tailing) or in a variety of other vectors (e.g. the Okayama-Berg cDNA cloning vectors, Messing cDNA cloning vectors and the like). Specific cDNA molecules in a vector in said library is then selected by using specific oligonucleotides designed, based on amino acid sequences contained within P40, to encode at least part of said sequence. Particularly useful is the internal, partial amino acid sequence of P40 obtained after cyanogen bromide treatment which comprises:

$NH_2$—Ala Gly Asn Thr Leu Ser Phe Leu Lys Ser Leu

Leu Gly Thr Phe Gln Lys Thr Glu.

Oligonucleotide sequences based on the foregoing amino acid sequence are particularly useful in identifying cDNA clones encoding P40 or its derivatives. Once identified, cDNA molecules encoding all or part of recombinant LCC are then ligated into expression vectors. Additional genetic manipulation is routinely carried out to maximize expression of the cDNA in the particular host employed. The cDNA sequence encoding P40 is set forth below with the corresponding amino acid sequence:

```
                           -18                              -10
                   Met Leu Val Thr Tyr Ile Leu Ala Ser Val Leu Leu Phe Ser Ser
5' CAGACTCCCGTCAACATGTTGGTGACATACATCCTTGCCTCTGTTTTGCTCTTCAGTTCT 1                                                100
Val Leu Gly Gln Arg  Cys Ser  Thr Thr Trp Gly Ile Arg Asp Thr Asn Tyr Leu Ile Glu
GTGCTGGGCCAGAGA TGC AGCACCACATGGGGCATCAGAGACACCAATTACCTTATTGAA
                                                 100

20                                      30        ▼
Asn Leu Lys Asp Asp Pro Pro Ser Lys  Cys Ser  Cys Ser  Gly Asn Val Thr Ser  Cys Leu
AATCTGAAGGATGATCCACCGTCAAAA TGC AGC TGC AGCGGCAACGTGACCAGC TGC TTG 40                              50
 Cys Leu Ser Val Pro Thr Asp Asp  Cys Thr  Thr Pro  Cys Tyr Arg Glu Gly Leu Leu Gln
 TGT CTCTCCGTCCCAACTGATGAT TGT ACCACACCG TGC TACAGGGAGGGACTGTTACAG
 ▼                          200
```

-continued

```
            60                                          70
Leu  Thr  Asn  Ala  Thr  Gln  Lys  Ser  Arg  Leu  Leu  Pro  Val  Phe  His  Arg  Val  Lys  Arg  Ile
CT GAC CAA TGC CAC ACA GAA ATC AAG ACT CTT GCC TGT TTT CCA TCG GGT GAA AAG GAT A
                                                                                      300

80                     ▼                    90                           ▼
Val  Glu  Val  Leu  Lys  Asn  Ile  Thr  |Cys| Pro  Ser  Phe  Ser  |Cys| Glu  Lys  Pro  |Cys| Asn  Gln
GTT GAA GTC CTA AAG AAC ATC ACG |TGT| CCG TCC TTT TCC |TGC| GAA AAG CCA |TGC| AAC CAG 100                                         110
Thr  Met  Ala  Gly  Asn  Thr  Leu  Ser  Phe  Leu  Lys  Ser  Leu  Leu  Gly  Thr  Phe  Gln  Lys  Thr
ACC ATG GCA GGC AAC ACA CTG TCA TTT CTG AAG AGT CTC CTG GGG ACG TTC CAG AAG ACA
                                                                                      400

120                      126
Glu  Met  Gln  Arg  Gln  Lys  Ser  Arg  Pro
GAG ATG CAA AGG CAG AAA AGC CGA CCA TGA AGA CAG ATG CTA TTT ATT CTA TTT ATT GAA

TTT ACA AAA CCT CCC CTC CTT AAC TGT TAC AGT GAA GAA ATA AAC TAA GCT ATT CT 3'
                                   500
```

Accordingly, P40 is synthesized in vivo, inserting said cDNA sequence into an expression vector, transforming the resulting recombinant molecule into a suitable host and then culturing or growing the transformed host under conditions requisite for the synthesis of the molecule. The recombinant molecule defined herein should comprise a nucleic acid sequence encoding a desired polypeptide inserted downstream of a promoter, a eukaryotic or prokaryotic replicon and a selectable marker such as resistance to an antibiotic. The recombinant molecule may also require a signal sequence to facilitate transport of the synthesized polypeptide to the extracellular environment. Alternatively, the polypeptide may be retrieved by first lysing the host cell by a variety of techniques such as sonication, pressure dissintegration or toluene treatment. Hosts contemplated in accordance with the present invention can be selected from the group comprising prokaryotes (e.g., *Escherichia coli, Bacillus* sp., *Pseudomonas* sp.) and eukaryotes (e.g., mammalian cells, yeast and fungal cultures, insect cells and plant cultures). The artisan will also recognize that a given amino acid sequence can undergo deletions, substitutions and additions of nucleotides or triplet nucleotides (codons). Such variations are all considered within the scope of the present invention. Additionally, depending on the host expressing recombinant P40, said P40 may or may not be glycosylated. Generally, eukaryotic cells, for example mammalian T cells and the like, will glycosylate the recombinant P40. Prokaryotic cells, for example bacteria such as *Escherichia coli* and the like, will not glycosylate the recombinant P40. Both glycosylated and non-glycosylated P40 are encompassed by the present invention.

Another aspect of the present invention relates to the helper T cell lines which produce P40. As defined herein, P40 or compositions comprising same, stimulate the development of permanent antigen-independent T helper cell lines which are maintained by subcultivation every 3 to 4 days in medium with P40. Even more particularly, the present invention is directed to TS1, one of the factor-dependent cell lines derived from TUC2.15.

The following examples further illustrate the present invention.

EXAMPLE 1

Materials and Methods

Medium

Dulbecco's modified Eagle's medium supplemented with 10% (v/v) fetal bovine serum (FCS), 50 uM mercaptoethanol, 0.55 mM L-arginine, 0.24 mM L-asparagine and 1.25 mM L-glutamine are used for most cell lines except for 7TD1 and BCL1 which are grown in Iscove's medium.

T Cell Clones and Lines

Helper T cell lines are established and maintained in the absence of exogenous growth factors as described by Van Snick et al. *Proc. Natl. Acad. Sci. USA* 83:9679–9683, 1986. Lines TUC2 and TUC7 are derived from C57BL/6 mice immunized with keyhole limpet hemocyanin. Line TUC5 is obtained from the same strain of mice but after immunization with human transferrin. TUC13 is an allospecific BALB/c anti-C57BL/6 line. Individual clones are derived from these lines by limiting dilution in the presence of 10% (v/v) medium conditioned by rat spleen cells stimulated with concanavalin A, and are denoted TUCx.y (where x stands for the number of the line and y for the number of the clone). These clones are subsequently expanded and maintained without exogenous growth factors like the parental cell lines. Cytolytic T cell clones of DBA/2 origin directed against syngeneic P815 mastocytoma are maintained with 50% (v/v) mixed lymphocyte culture medium as described by Maryanski et al. *Eur. J. Immunol.* 12:401–406, 1982. For use in growth factor assays, the T cells are separated from feeder cells by centrifugation over a layer of Lymphoprep (Nycomed AS, Oslo, Norway) washed and incubated at 5×10⁴ cells/well. Proliferations are measured on day 3 after a 6 hr pulse with methyl-labeled {³H}-thymidine (0.5 uCi/well).

Preparation of Helper T Cell Supernatants

TUC2.15 and TUC7.51 cells, obtained from cultures stimulated 2 weeks earlier with antigen and feeder cells, are adjusted to 2×10⁶ cells/ml and incubated for 2–3 days in medium containing 0.5% (v/v) FCS and concanavalin A (ConA, 5 ug/ml). Supernatants (SN) are collected by centrifugation at 10,000 g for 20 min. When used for culture, crude SN are supplemented with 0.1 M methyl-α-D-mannoside.

TS1 Growth Factor Assay

Factor-dependent TS1 cells are cultured in 1% (v/v) TUC2.15 SN. Before use in the growth factor assay, the cells are washed free of SN and cultured at a density of $3\times 10^3$ cells/well in 200 ul with serial dilutions of samples to be tested. After 3 days, cell growth is measured by colorimetric determination of hexosaminidase levels according to Landegren *J. Immunol. Methods* 67:379–388, 1984. The dilution giving half-maximal absorbance at 405 nm is arbitrarily assigned one U/ml of activity.

Other Cell Lines

CTLL-2 (Gillis et al., *J. Immunol.* 120:2027–2032, 1978) is grown with 100 U/ml of human recombinant IL-2 DA-1 (Ihle et al. *Adv. Viral Oncol.* 4:95–137, 1984), Ea3.15 (Palacios et al. Nature 309:126–131, 1984), FDC-P1 (Dexter et al. *J. Exp. Med.* 152:1036–1047, 1980) with 10% (v/v) WEHI-3 SN as a source of IL3 and 7TD1 with a 1/500 dilution of TUC2.15 SN as a source of IL6 (Van Snick et al. supra). Assays using these cell lines are carried out as described for the TS1 line and proliferations are measured either by hexosaminidase determinations or by thymidine incorporation. In vivo passaged BCL1 cells (Slavin et al. *Nature* 272:624–626, 1978) are frozen in aliquots and thawed just before use. Proliferation of BCL1 is measured by thymidine incorporation in 7 day-old cultures seeded with $10^4$ cells/well.

Cytokines and Growth Factors

Purified natural human IL1 β (Van Damme et al., Nature 314:226–268, 1985), recombinant human IL2 (Devos et at. *Nucl. Acids Res.* 11:4307–4323) and purified murine IL3 (Ihle et al. *J. Immunol.* 129:2431–2436, 1982) are as described. Human recombinant granulocyte colony-stimulating factor (G-CSF) and mouse recombinant granulocyte-macrophage colony stimulating factor (GM-CSF) is described by DeLamarter et al. *Embo J.* 4:2575–2581, 1985. Platelet-derived growth factor (PDGF) is described by Heldin et al. *Proc. Natl. Acad. Sci. USA* 76:3722–3726, 1979. Epidermal growth factor (EGF) is purchased from Boehringer (Mannheim, Fed. Rep. Germany). Mouse IL4, IL5 and IL6 are purified as described by Van Snick, supra, and Vink et al. *Eur. J. Immunol.* 18:607–612 1988.

Antibodies

Anti-IL4 antibody 11B11 (Ohara et al. *Nature* 315:333–336, 1985) and anti-IL2 receptor antibody 5A2 (Moreau et al. *Eur. J. Immunol.* 17:929–935, 1987) are as described. *Purification of TS1 Growth Factor*

Adsorption to silicic acid and gel filtration is performed as described (Van Snick supra). Active fractions from the gel filtration column are pooled, concentrated by ultrafiltration on an Amicon YM-10 membrane in the presence of $10^{-4}$ (v/v) dilution of Tween 20 and transferred to 1 M Na$_2$SO$_4$ buffered to pH 7.0 with 0.1 M sodium phosphate before injection onto a TSK-Phenyl column (LKB, Bromma, Sweden) equilibrated in the same buffer. After a 10 min wash in the starting buffer, elution is carried out at 0.6 ml/min with a linear gradient of a 1:1 mixture of a sodium phosphate buffer (0.1 M pH 7.0) and ethylene glycol. Active fractions are further fractionated on a MonoQ column (Pharmacia, Fin Chemicals, Uppsala, Sweden) equilibrated in 20 mM ethanolamine-HCl pH 9.5, 20 mM NaCl and $10^{-4}$ (v/v) Tween 20. The column is developed at 0.8 ml/min with a 30 min linear gradient of NaCl (8 mM/min). Pooled active fractions are concentrated and adjusted to contain 0.05% (w/v) trifluoroacetic acid (TFA) before injection on a Cl 25-nm pore-size TSK TMS-250 HPLC column (LKB). The column is developed for the first 10 min with a linear gradient from 0 to 35% (w/v) acetonitrile in 0.05% (w/v) TFA, which is followed by a shallow 35–36% gradient for the next 60 min. Flow rate is adjusted to 0.8 ml/min; 1 min fractions are collected in Eppendorf tubes containing 10 ul of 1 M NH$_4$HCO$_3$ and 5 ul of Tween 20 (1% (v/v) in water) and lyophilised. Total protein is measured fluorometrically with benzoxanthene following Neuhoff et al. *Hoppe-Seyler's Z. Physiol. Chem.* 360:1657–1670, 1979. The purity of the final product is assessed by NaDodSO$_4$/PAGE in 12% (w/v) acrylamide gels. Isoelectric focusing is performed with a LKB (Bromma, Sweden) vertical gel apparatus. Material is recovered from gels by overnight incubation in 130 mM NaCl containing Tween 20 ($10^{-4}$ v/v) and 10 mM sodium phosphate pH7.0. Affinity chromatography on lentil lectin-Sepharose is done following the procedure described by the manufacturer (Pharmacia, Uppsala, Sweden).

Amino Acid Sequence Analysis

Automated amino acid sequence analysis is performed with an Applied Biosystems sequencer (model 477A) equipped with an on-line phenylthiohydantoin amino acid analyzer (model 120A). In situ cyanogen bromide cleavage of P40 ($\approx$10 ug) is performed on the glass fiber sample disk of the gas-phase sequencer according to a procedure described by Simpson et al. *Biochem. Internat.* 8:787–791, 1984. Sequence comparisons are made with the following databases: Protein Sequence database of PIR, National Biomedical Research Foundation (release 15.0, December 1987); Swiss-Prot Protein Sequence Data Bank version 5 (September 1987, compiled by A. Bairoch, University of Geneva, Medical Biochemistry Department, 1211 Geneva 4, Switzerland); G.B. trans Protein Data Base Release 1.0 (August 1987) compiled from GENBANK release 50.0 by J. Coventry, Walter and Eliza Hall Institute of Medical Research, Parkville 3050 Australia; and PG trans Protein Data Base release 38.0 (December 1985) GENBANK, Instit. Pasteur, Paris, France.

EXAMPLE 2

Detection of T Cell Growth Factor Activity

TUC2.15 is a C57B1/6 helper T cell line that requires antigen and antigen-presenting cells for long term growth in vitro. In an attempt to grow these cells without feeders and antigens it is surprisingly discovered that, after supplementing the culture medium with 10% (v/v) autologous supernatant (SN) obtained after stimulation with ConA, this SN is able to induce cell proliferation without further requirement for antigen or feeder cells. This growth factor activity is not inhibited by either anti-IL4 or anti-IL2 receptor antibodies (Table 1), indicating that the activity is mediated neither directly nor indirectly by these molecules.

Figure 1:
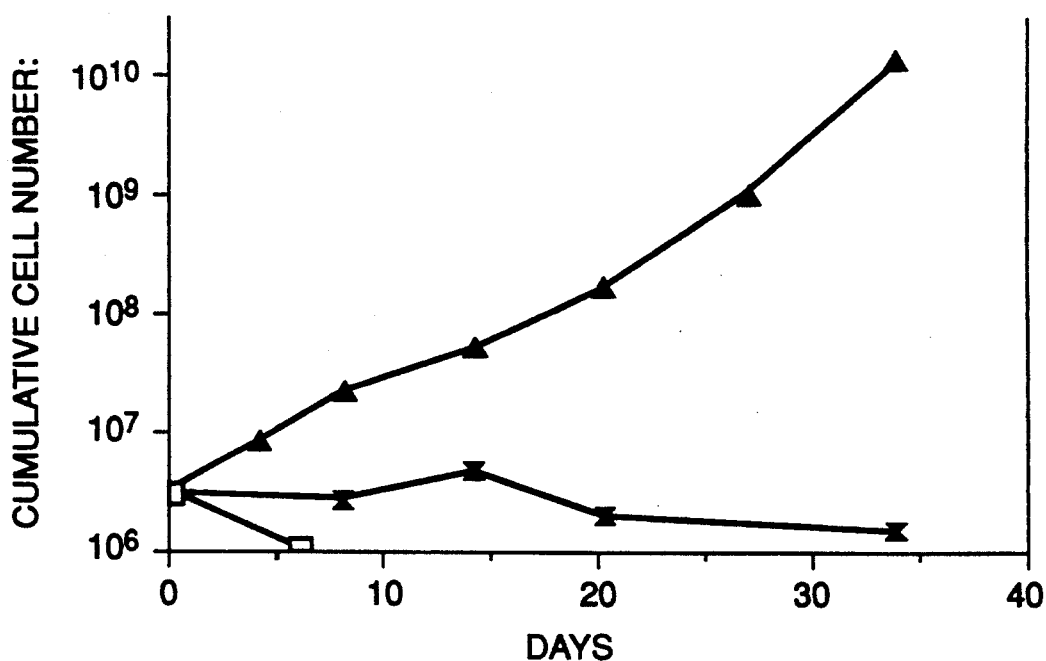
FIG. 1 is a graphical representation depicting long term antigen-independent T cell growth induced by helper T cell supernatant (SN). TUC2.15 cells are grown without feeder cells and antigen in normal medium (□), in medium supplemented with IL2 (20U/ml, ■) or with TUC2.15 SN (5% v/v, ▲).

In addition to its activity in short term proliferations, the SN also readily stimulates the development of permanent antigen-independent cell lines, which are maintained by subcultivation every 3–4 days in medium supplemented with 1% (v/v) SN (FIG. 1). Attempts to derive antigen-independent cells lines with IL2 in this manner are to date unsuccessful. A second helper T cell clone, TUC7.51 also gives rise to an antigen-independent cell line upon culture in autologous SN. The factors active on the two cell lines are apparently identical, since TUC7.51 SN supported the growth of TUC2.15 cells and vice versa.

TS1, one of the factor-dependent cell lines derived from TUC2.15 is selected for further identification of the growth factor. This choice is based on the observation that TS1 grows quickly, with a doubling time of 11 h, and responds to very small concentrations of SN, half-maximal proliferation being obtained at dilutions between $10^{-5}$ and $10^{-4}$ (v/v). To determine the specificy of the TS1 assay, cells are incubated with a variety of purified growth factors or crude SN and found that only IL4 and TUC2.15 SN support TS1 growth (Table 2). Since anti-IL4 antibodies fail to inhibit the effects of TUC2.15 SN, the aforementioned activity is a new T cell growth factor.

TABLE 1

Proliferation of TUC2.15 Helper T Cells Induced By Autologous Supernatant (SN); Independence from IL2 and IL4

| Antibodies Added | Proliferation in response to | | |
|---|---|---|---|
| | IL2 | IL4 | TUC2.15 SN |
| | (kepm) | | |
| none | 152 | 18 | 37 |
| anti-IL2 receptor | 4 | 16 | 32 |
| anti-IL4 | 156 | 1 | 33 |

TUC2.15 helper T cells ($5 \times 10^4$/well) are incubated for 3 days with IL2 (100 U/ml), IL4 (100 U/ml) or TUC2.15 SN (1% v/v) in the presence of anti-IL2 receptor antibody 5A2 (30 ug/ml) or anti-IL4 antibody 11B11 (10 ug/ml). Thymidine incorporation is measured on day 3.

TABLE 2

Growth of TS1 in Response to Various Cytokines

| Factors | Dose/Dilution | Cell Growth ($A^{405}$) |
|---|---|---|
| TUC2.15 SN | 1/12.500 | 1.96 |
| IL1· | 100 U/ml | 0 |
| IL2 | 100 U/ml | 0 |
| IL3 | 100 U/ml | 0.01 |
| IL4 | 100 U/ml | 1.36 |
| IL5 | 100 U/ml | 0 |
| IL6 | 20 ng/ml | 0 |
| GM-CSF | 10 ng/ml | 0 |
| G-CSF | 4 ng/ml | 0 |
| M-CSF (crude) | 1/4 | 0.02 |
| EGF | 50 ng/ml | 0 |
| PDGF | 4 ug/ml | 0.02 |

TS1 cells are incubated for 3 days in the presence of various factors or SN. All reagents are tested over a 100-fold range but results are given for the highest dose only. None of the factors that score negatively at the highest dose have any effect at lower doses. Cell growth is measured by colorimetric determination of hexosaminidase levels. Absorbance (A) of cultures at 405 nm incubated without growth factors ranges from about 0.10 to about 0.15 and is subtracted.

EXAMPLE 3

Purification of the T Cell Growth Factor

Large batches of T cell SN are produced by stimulating TUC2.15 and TUC7.51 cells with ConA as described in Example 1. The active material is concentrated by adsorption to silicic acid and applied to an Ultrogel AcA54 gel filtration column. The major growth promoting activity, which is destroyed by trypsin, elutes as a symmetrical peak in the 30-40 kDa region (FIG. 2A), and is therefore designated P40. Subsequent experiments are carried out with TUC7.51 SN because the concentrations of P40 are higher in this material.

Figure 2A:
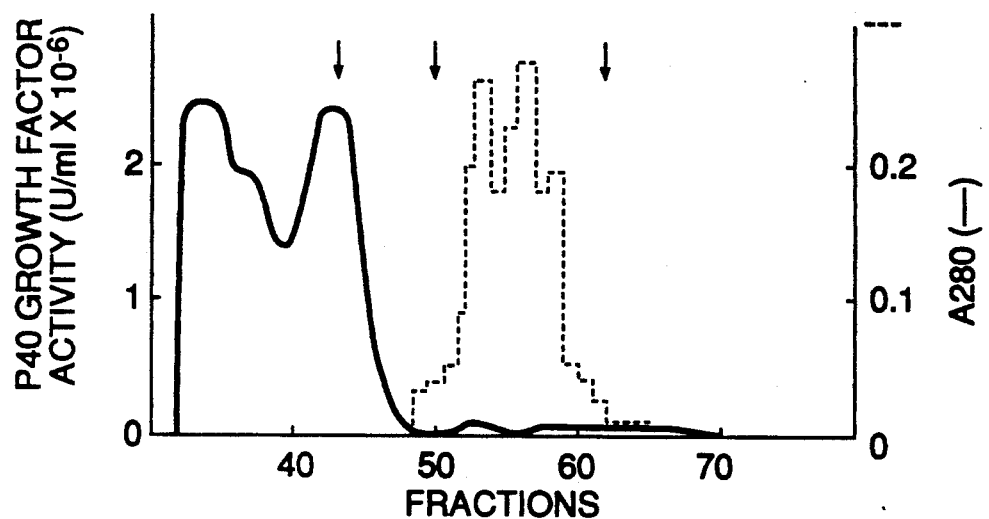
FIG. 2(A) shows purification of P40 TUC7.51 on the AcA54 gel filtration column. Molecular mass standards are bovine serum albumin (BSA, 67 KDa) and natural IL5 (45 KDa) recombinant mouse IL-6 (22 KDa).
Figure 2B:
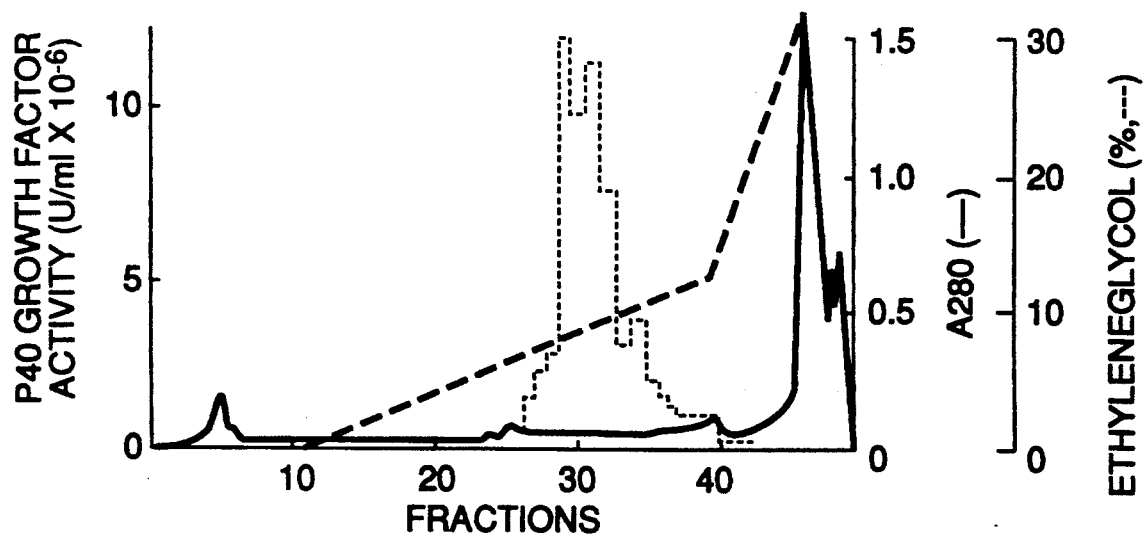
FIG. 2B depicts purification of the product of $A_cA54$ gel filtration, on a TSK-phenyl hydrophobic interaction column.
Figure 2C:
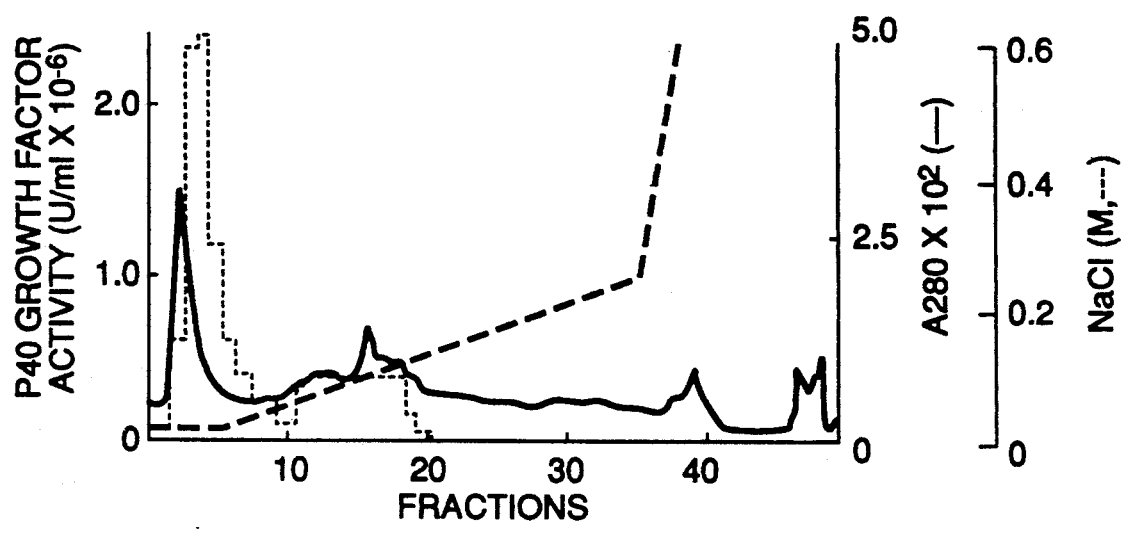
FIG. 2(C) presents the filtration of the product of the filtration shown in 2(B), on a Mono-Q anion exchange column.
Figure 2D:
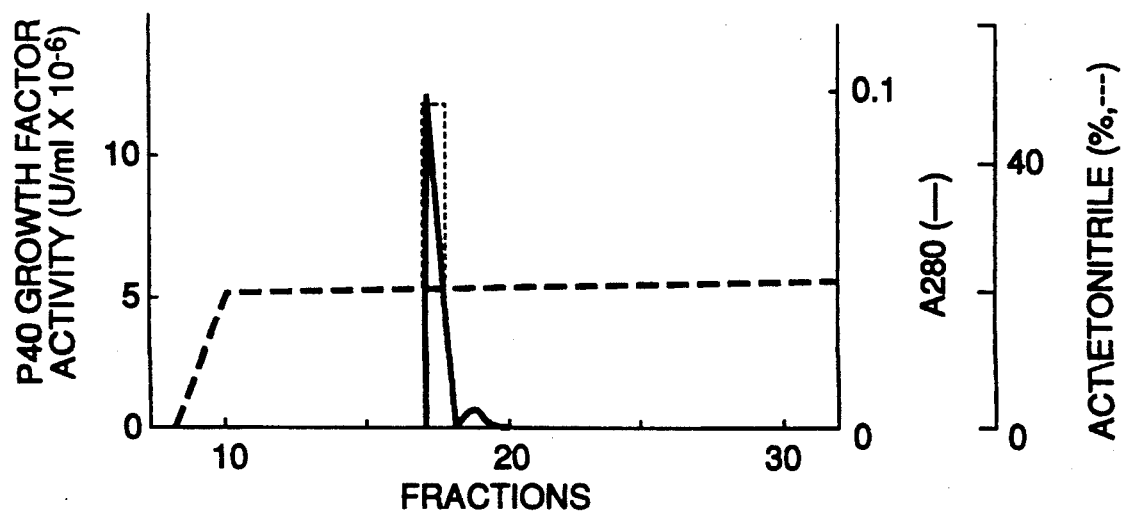
FIG. 2(D) depicts purification of the filtrate of 2(C), on a C1-reversed phase column.

Preliminary characterization of the growth factor indicates that it had a pI of 10 and is glycosylated, 60% of the activity being retained on a lentil lectin column. Based in part on this information, the following purification protocol is adopted. Active fractions from the gel filtration step are further separated by hydrophobic interaction chromatography on a TSK-phenyl column (FIG. 2B) followed by passage through a MonoQ anion exchange column equilibrated at pH 9.5. At this elevated pH, most contaminants are retained on the column, whereas P40 elutes mainly in the flow-through fractions, as expected from its high pI (FIG. 2C). Final purification is achieved by reversed phase chromatography on a C1-column equilibrated with 0.05% (w/v) TFA. P40 is recovered in a single peak eluting at an acetonitrile concentration of 35% (v/v) (FIG. 2D). At the end of this purification, P40 stimulates half-maximal growth of TS1 at a concentration of 5 pg/ml (FIG. 3), which corresponds to a 2000-fold purification. On average, the overall yield ranges from about 5 to about 10%.

The purified protein is very heterogeneous with a Mr of about 32 to about 39 kDa in NaDodSO4/ PAGE both under reducing (FIG. 4) and non-reducing conditions. Biological activity is recovered from the corresponding fractions of a non-reduced gel, but exposure to NaDodSO4 and 2-mercaptoethanol destroys most of the activity.

EXAMPLE 4

Amino Acid Sequence Analysis of P40

Edman degradation of P40 ($\approx$250 pmol) did not yield N-terminal sequence. For sequence analysis, P40 (immobilized on the polybrene-treated sample disk of the sequencer) is acylated (Tarr, Methods of Protein Microcharacterization [ed. J. E. Shively] Human Press, pp. 155-194, 1986) and then subjected to in situ cyanogen bromide treatment as described by Simpson surpa. Sequence analysis is then continued and yields the following major amino acid sequence (110 pmol): NH2-Ala Gly Asn Thr Leu Ser Phe Leu Lys Ser Leu Leu Gly Thr Phe Gln Lys Thr Glu.

This internal sequence shows no significant similarity with that of other proteins stored in the data bases listed in Example 1.

Subsequent to the determination of the partial internal amino acid sequence, the entire sequence is determined to be as follows:

```
                                         -18                                            -10
                                         Met Leu Val Thr Tyr Ile Leu Ala Ser Val Leu Leu Phe Ser Ser
5' CAGACTCCCGTCAACATGTTGGTGACATACATCCTTGCCTCTGTTTTGCTCTTCAGTTCT
```

```
       1                                                                           100
Val Leu Gly Gln Arg Cys Ser Thr Thr Trp Gly Ile Arg Asp Thr Asn Tyr Leu Ile Glu
GTGCTGGGCCAGAGA TGC AGCACCACATGGGGCATCAGAGACACCAATTACCTTATTGAA
                                                  100

20                                30                              ▼
Asn Leu Lys Asp Asp Pro Pro Ser Lys Cys Ser Cys Ser Gly Asn Val Thr Ser Cys Leu
AATCTGAAGGATGATCCACCGTCAAAA TGC AGC TGC AGCGGCAACGTGACCAGC TGC TTG 40                                     50
Cys Leu Ser Val Pro Thr Asp Asp Cys Thr Thr Pro Cys Tyr Arg Glu Gly Leu Leu Gln
TGT CTCTCCGTCCCAACT GAT GAT TGT ACCACACCG TGC TACAGGGAGGGACTGTTACAG
           ▼            200

60                                     70
Leu Thr Asn Ala Thr Gln Lys Ser Arg Leu Leu Pro Val Phe His Arg Val Lys Arg Ile
CTGACCAATGCCACACAGAAATCAAGACTCTTGCCTGTTTTCCATCGGGTGAAAAGGATA
                                                                          300

80          ▼                              90                          ▼
Val Glu Val Leu Lys Asn Ile Thr Cys Pro Ser Phe Ser Cys Glu Lys Pro Cys Asn Gln
GTTGAAGTCCTAAAGAACATCACG TGT CCGTCCTTTTCC TGC GAAAAGCCA TGC AACCAG 100                                 110
Thr Met Ala Gly Asn Thr Leu Ser Phe Leu Lys Ser Leu Leu Gly Thr Phe Gln Lys Thr
ACCATGGCAGGCAACACACTGTCATTTCTGAAGAGTCTCCTGGGGACGTTCCAGAAGACA
                                                             400

120              126
Glu Met Gln Arg Gln Lys Ser Arg Pro
GAGATGCAAAGGCAGAAAAGCCGACCATGAAGACAGATGCTATTTATTCTATTTATTGAA

TTTACAAAACCTCCCCTCCTTAACTGTTACAGTGAAGAAATAAACTAAGCTATTCT 3'
         500
```

EXAMPLE 5

Biological Activity of Purified P40

Purified P40, at concentrations up to 20 ng/ml, did not support the proliferation of either IL3-dependent myeloid cell lines (FDCP-1, Ea3.15 and DA-1), IL5-dependent B cell lymphoma BCL1, or IL6-dependent B cell hybridoma 7TD1. Unlike IL2, and to some extent IL4, it also fails to stimulate any of six cytolytic T cell clones tested (Table 3). By contrast, strong proliferations are observed with some but not all helper T cell lines. Both IL2-producing (TH₁ type, TUC7.33) and IL4-producing (TH₂ type, e.g., TUC2.15) clones are found among the responders. A significant correlation, illustrated in Table 3 for clone TUC7.51, is observed between the time spent in culture and the responses to P40 and IL4.

TABLE 3

Comparison of the T Cell Growth Factor Activities of IL2, IL4, and Purified P40

| T Cell Lines and Clones | | Proliferation in response to[a] | | |
|---|---|---|---|---|
| | | IL2 | IL4 | P40 |
| Cytolytic T Cells | CTLL-2 | 445 | 0.6 | 0.8 |
| | P35:10 | 683 | 24 | 1.2 |
| | P35:48 | 303 | 4 | 1.8 |
| | P91:6 | 195 | 2 | 1.6 |
| | P1:5 | 993 | 12 | 1.2 |
| | P1:204-8 | 630 | 9 | 1.2 |
| Helper T Cells | TUC2 | 311 | 2 | 14 |
| | TUC2.15 | 1,806 | 813 | 240 |
| | TUC5 | 263 | 20 | 13 |
| | TUC5.37 | 253 | 4 | 0.8 |

TABLE 3-continued

Comparison of the T Cell Growth Factor Activities of IL2, IL4, and Purified P40

| T Cell Lines and Clones | Proliferation in response to[a] | | |
|---|---|---|---|
| | IL2 | IL4 | P40 |
| TUC7.33 | 115 | 276 | 235 |
| TUC7.51[b] | 1,179 | 27 | 17 |
| TUC7.51[c] | 1,345 | 634 | 199 |
| TUC13.1 | 116 | 51 | 1.7 |

[a] Cells are incubated with or without the indicated growth factors and thymidien incorporation is measured on day 3. Factor dosage is as follows: 100 U/ml for IL2 and IL4, and 10³–10⁴ U/ml for P40. The results are shown as ratios of radioactivity incorporated with and without factors.
[b] 1 month-old culture
[c] 1 year-old culture

What is claimed is:

1. An isolated biologically pure, mammalian T cell growth factor molecule which is a single chain glycoprotein having a molecular weight of from about 30 KDa to about 40 KDa and which supports interleukin-2 and interleukin-4 independent growth of helper T cells.

2. The isolated biologically pure mammalian T cell growth factor molecule of claim 1, wherein said molecule has partial internal amino acid sequence:

H₂N—Ala—Gly—Asn—Thr—Leu—Ser—Phe—Leu—Lys—

Ser—Leu—Leu—Gly—Thr—Phe—Gln—Lys—Thr—Glu.

3. The biologically pure mammalian T cell growth factor molecule of claim 1, having amino acid sequence:

```
             −18                                          −10
             Met Leu Val Thr Tyr Ile Leu Ala Ser Val Leu Leu Phe Ser Ser
5' CAGACTCCCGTCAACATGTTGGTGACATACATCCTTGCCTCTGTTTTGCTCTTCAGTTCT
```

-continued

```
        1                                                100
Val Leu Gly Gln Arg Cys Ser Thr Thr Trp Gly Ile Arg Asp Thr Asn Tyr Leu Ile Glu
GT GCT GGG CCA GAG A TGC AGC ACC ACA TGG GGC ATC AGA GAC ACC AAT TAC CTT ATT GAA
                                                    100

20                                   30
Asn Leu Lys Asp Asp Pro Pro Ser Lys Cys Ser Cys Ser Gly Asn Val Thr Ser Cys Leu
AAT CTG AAG GAT GAT CCA CCG TCA AAA TGC AGC TGC AGC GGC AAC GTG ACC AGC TGC TTG 40                              50
Cys Leu Ser Val Pro Thr Asp Asp Cys Thr Thr Pro Cys Tyr Arg Glu Gly Leu Leu Gln
TGT CTC TCC GTC CCA ACT GAT GAT TGT ACC ACA CCG TGC TAC AGG GAG GGA CTG TTA CAG
                        200

60                                   70
Leu Thr Asn Ala Thr Gln Lys Ser Arg Leu Leu Pro Val Phe His Arg Val Lys Arg Ile
CT GAC CAA TGC CAC ACA GAA ATC AAG ACT CTT GCC TGT TTT CCA TCG GGT GAA AAG GAT A
                                                                         300

80                                   90
Val Glu Val Leu Lys Asn Ile Thr Cys Pro Ser Phe Ser Cys Glu Lys Pro Cys Asn Gln
GTT GAA GTC CTA AAG AAC ATC ACG TGT CCG TCC TTT TCC TGC GAA AAG CCA TGC AAC CAG 100                          110
Thr Met Ala Gly Asn Thr Leu Ser Phe Leu Lys Ser Leu Leu Gly Thr Phe Gln Lys Thr
ACC ATG GCA GGC AAC ACA CTG TCA TTT CTG AAG AGT CTC CTG GGG ACG TTC CAG AAG ACA
                                                                    400

120              126
Glu Met Gln Arg Gln Lys Ser Arg Pro
GAG ATG CAA AGG CAG AAA AGC CGA CCA TGA AGA CAG ATG CTA TTT ATT CTA TTT ATT GAA

TTT ACA AAA CCT CCC CTC CTT AAC TGT TAC AGT GAA GAA ATA AAC TAA GCT ATT CT 3'
                500
```

4. The biological pure, mammalian T cell growth factor molecule of claim 1, wherein said molecule is a human T cell growth factor.

5. The biologically pure, mammalian T cell growth factor molecule of claim 1, wherein said molecule is a murine T cell growth factor.

6. A composition useful in inducing proliferation of helper T cells in vitro comprising an amount of the biologically pure, protein containing T cell growth factor molecule of claim 1 sufficient to induce helper T cell proliferation and a pharmaceutically acceptable carrier.

* * * * *